(12) United States Patent
Orthner et al.

(10) Patent No.: US 8,310,682 B2
(45) Date of Patent: Nov. 13, 2012

(54) APPARATUS, SYSTEM AND METHODS FOR ANALYZING PRESSURE-SENSITIVE DEVICES

(75) Inventors: Michael Orthner, Salt Lake City, UT (US); Florian Solzbacher, Salt Lake City, UT (US); Loren Rieth, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 175 days.

(21) Appl. No.: 12/933,597

(22) PCT Filed: Mar. 20, 2009

(86) PCT No.: PCT/US2009/037833
§ 371 (c)(1),
(2), (4) Date: Dec. 16, 2010

(87) PCT Pub. No.: WO2009/117674
PCT Pub. Date: Sep. 24, 2009

(65) Prior Publication Data
US 2011/0122419 A1    May 26, 2011

Related U.S. Application Data

(60) Provisional application No. 61/038,306, filed on Mar. 20, 2008.

(51) Int. Cl.
*G01B 11/24* (2006.01)
(52) U.S. Cl. ...................................... 356/601
(58) Field of Classification Search .......... None
See application file for complete search history.

(56) References Cited

U.S. PATENT DOCUMENTS

| 4,733,553 A | 3/1988 | Folk et al. |
| 4,777,716 A | 10/1988 | Folk et al. |
| 5,668,305 A | 9/1997 | Chi et al. |

(Continued)

FOREIGN PATENT DOCUMENTS

WO    WO 98/34092    8/1998

(Continued)

OTHER PUBLICATIONS

Mitchell et al.; Examination of Bulge Test for Determining Residual Stress, Young's Modulus, and Poisson's Ration of 3C-SiC Thin Films; Journal of Aerospace Engineering; Apr. 2003; pp. 46-54.

(Continued)

*Primary Examiner* — Tu Nguyen
(74) *Attorney, Agent, or Firm* — Thorpe North & Western LLP (57) ABSTRACT

A testing and analysis system for a pressure-sensitive device (42) that includes a testing stage (10) comprising a platform having a groove situated on an upper surface, an endless support gasket located in the endless groove, a pressure port located on the upper surface and interior to the endless groove, and a means for securing a substrate above the upper surface. The substrate (40) supports a pressure-sensitive device (42) to form a pressure chamber between the substrate (40) and the upper surface. A pressure source (32) is operatively connected to the pressure port to modify a pressure inside the pressure chamber and deflect the pressure-sensitive device (42). A surface profile measurement apparatus (104) is included for measuring a surface profile of the deflected pressure-sensitive device (42).

20 Claims, 6 Drawing Sheets

U.S. PATENT DOCUMENTS

| | | | |
|---|---|---|---|
| 5,677,477 A | 10/1997 | Man et al. | |
| 5,741,975 A * | 4/1998 | Vaughn et al. | 73/706 |
| 6,373,271 B1 | 4/2002 | Miller et al. | |
| 6,422,370 B1 * | 7/2002 | Thomire | 192/85.51 |
| 6,688,156 B2 | 2/2004 | Dietrich et al. | |
| 7,174,773 B2 | 2/2007 | Borzabadi et al. | |
| 7,311,009 B2 | 12/2007 | Kotovsky | |
| 2005/0116729 A1 | 6/2005 | Koester et al. | |
| 2005/0121615 A1 | 6/2005 | Prater et al. | |
| 2007/0245808 A1 | 10/2007 | Henttonen et al. | |

FOREIGN PATENT DOCUMENTS

| | | |
|---|---|---|
| WO | WO 01/98793 | 12/2001 |
| WO | WO 2009/117674 | 9/2009 |

OTHER PUBLICATIONS

PCT Application PCT/US2009/037833; filed Mar. 20, 2009; Michael Orthner; International Search Report issued Nov. 5, 2009.

* cited by examiner

APPARATUS, SYSTEM AND METHODS FOR ANALYZING PRESSURE-SENSITIVE DEVICES

RELATED APPLICATIONS

This application claims priority to U.S. Provisional Application Ser. No. 61/038,306, filed Mar. 20, 2008, and entitled "Apparatus, System and Methods for Analyzing Pressure-Sensitive Devices", which application is incorporated by reference in its entirety herein.

BACKGROUND OF THE INVENTION

Numerous technologies have been developed for characterizing surfaces and surface properties. In particular, contact and non-contact profilometers make possible the measurement of surface profiles with resolutions down to the nanometer level. One application of this technology lies in analyzing the characteristics and performance of microdevices. These devices are commonly used as components in microscale fluidics and electronics systems. A number of them, such as diaphragms and thin-film membranes, are designed to be particularly sensitive to small pressure changes and serve as actuators, switches, flow detectors, and the like. More complete characterization of such devices can be facilitated by analyzing their responses to pressure under controlled conditions.

BRIEF DESCRIPTION OF THE DRAWINGS

Features and advantages of the present invention will be apparent from the detailed description that follows, and when taken in conjunction with the accompanying drawings together illustrate, by way of example, features of the invention. It will be readily appreciated that these drawings merely depict representative embodiments of the present invention and are not to be considered limiting of its scope, and that the components of the invention, as generally described and illustrated in the figures herein, could be arranged and designed in a wide variety of different configurations. Nonetheless, the present invention will be described and explained with additional specificity and detail through the use of the accompanying drawings, in which.

DETAILED DESCRIPTION OF EXEMPLARY EMBODIMENTS

The following detailed description of representative embodiments of the present invention makes reference to the accompanying drawings, which form a part hereof and in which are shown, by way of illustration, various representative embodiments in which the invention can be practiced. While these embodiments are described in sufficient detail to enable those skilled in the art to practice the invention, it should be understood that other embodiments can be realized and that various changes can be made to the invention without departing from the spirit and scope of the present invention. As such, the following detailed description of the representative embodiments is not intended to limit the scope of the invention as it is claimed, but rather is presented for purposes of illustration, to describe the features and characteristics of the present invention, and to sufficiently enable one skilled in the art to practice the invention. Accordingly, the scope of the present invention is to be defined solely by the appended claims.

Definitions

It is also to be understood that the terminology used herein is used for the purpose of describing particular embodiments only and is not intended to be limiting. In describing and claiming the present invention, the following terminology will be used.

The singular forms "a", "an", and "the" include plural referents unless the context clearly dictates otherwise.

Various embodiments of the present invention involve the application or maintenance of pressure to devices. As used herein, application of "positive pressure" refers to a pressure that increases the air pressure in a defined space or impinging on a surface of interest. This may involve raising said pressure to a level above local atmospheric pressure. However, in some applications, an increase in the already existing pressure in the space is sufficient. Conversely, application of "negative pressure" refers to a pressure that decreases the air pressure in a defined space or impinging on a surface of interest relative to an existing pressure with a confined volume.

The term "pressure-sensitive device" refers to any device that is sensitive to static pressure or to changes in pressure, such that these cause some discernable change in a physical property of the device. Most often these devices are piezoelectric resistors where electrical resistance changes as a function of mechanical deformation.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Embodiments of the Invention

Figure 1:
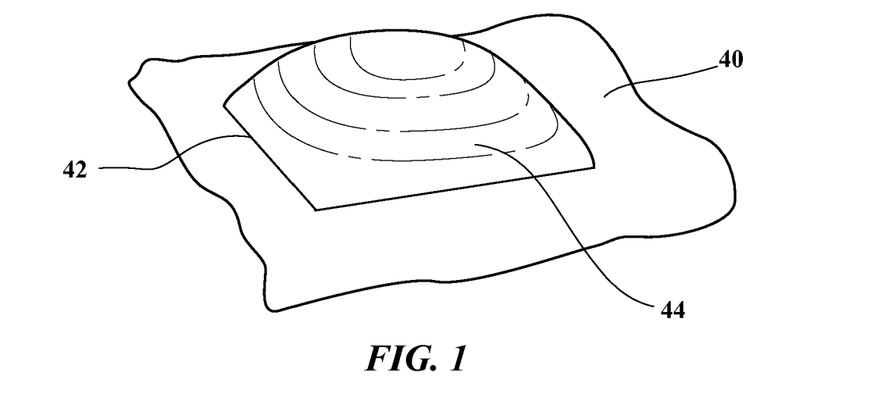
FIG. 1 illustrates a perspective view of a pressure-sensitive device undergoing testing, in accordance a representative embodiment of the present invention.

While profilometers provide the needed sensitivity and resolution for such analysis, these same instruments typically lack any provision for applying pressure or vacuum to the individual microdevices or to the semiconductor wafers or substrates containing such devices. Fabrication and quality control of systems employing pressure-sensitive devices can be improved by methods and apparatus for characterizing these devices under differing pressure conditions. It has been recognized that apparatus and methods are needed for analyzing pressure-sensitive devices while applying pressures to those devices. In light of this recognition and in accordance with a representative embodiment of the present invention, a system for the testing and analysis of pressure-sensitive devices or microdevices is provided. As shown in FIG. 1, the pressure-sensitive devices 42 or microdevices can include a diaphragm, a thin film membrane or a semiconductor substrate layer with a thin film applied thereto, etc., and can be supported and/or manufactured on a substrate or semiconductor wafer 40. The pressure sensitive device 42 can have a substantially planar structure that is sufficiently thin and flexible so that the device deflects in response to a pressure differential applied across the upper and lower surfaces of the device.

Pressure-sensitive devices 42 amenable to such testing include thin diaphragms, that can serve as components in piezoelectric and piezoresistive elements such as actuators, switches, and transducers. These devices are typically fabricated by applying various techniques to wafers of material, usually silicon, such as by ion implantation, chemical or physical deposition, separate fabrication and bonding, and the like. Pressure applied to such devices cause physical deformations that can be imaged, characterized, and measured to provide insights into the performance properties of the device, i.e. quality control, reliability, and/or performance testing. The degree of displacement of the deflected surface 44 in response to a known pressure differential can be directly proportional to the mechanical properties and structure design of the pressure-sensitive device, and can be fine-tuned to provide a variety of useful applications.

Figure 2:
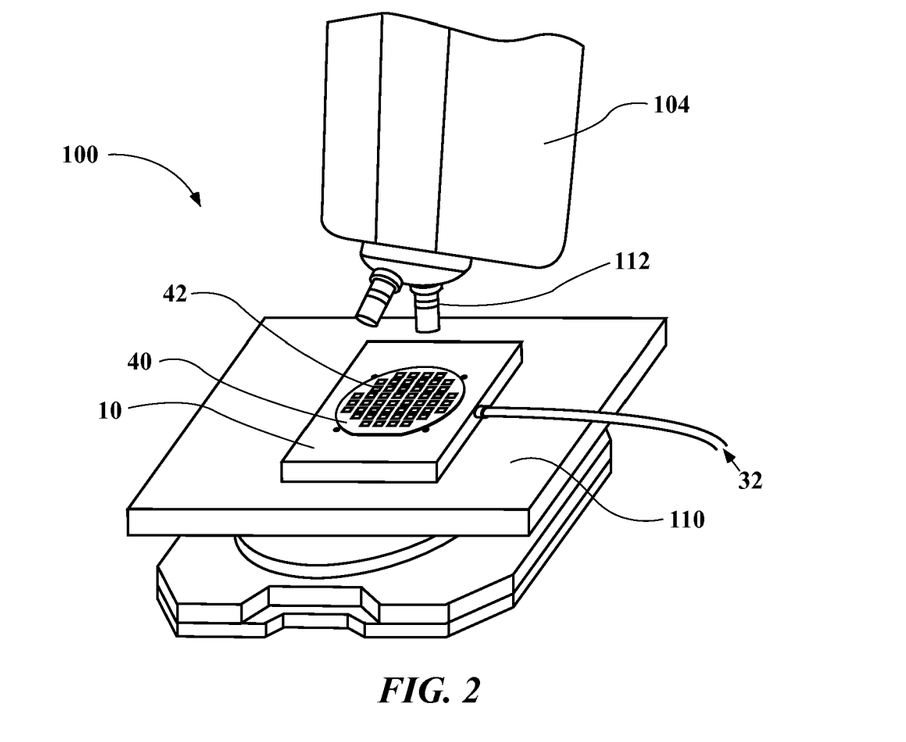
FIG. 2 illustrates a perspective view of a system for testing a pressure-sensitive device, in accordance with a representative embodiment of the present invention.

The testing and analysis system 100 illustrated in FIG. 2 can include a surface profile measurement apparatus 104 means for measuring the profile of the outer surface 44 (FIG. 1) of the deflected pressure sensitive device 42. In a representative embodiment, the surface profile measurement apparatus 104 can comprise a non-contacting optical profilometer, such as the optical profilometers currently supplied to the MEMS/Semiconductor industry by such manufacturers as Zygo, Metris and UBM. Other representative embodiments can include alternative means for measuring the surface profile, such contacting profilometers, including diamond stylus profilometers, and contact/pseudo-contact technologies, including atomic force microscopy and scanning tunneling microscopy.

The system 100 can provide for removably coupling the substrate or wafers 40 supporting one or more pressure-sensitive devices 42 to a testing stage 10. In turn, the assembled testing stage 10 and wafer 40 can be attached to a moveable test stand 110 located proximate to the surface profile measurement apparatus 104, the position of which can be precisely controlled to locate and align the various pressure-sensitive devices 42 with the optical sensor 112 of the surface profile measurement apparatus 104. Furthermore, the measurement process can be substantially automated, so that the test stand can automatically index to a new position and align with a different pressure-sensitive device prior to taking a new surface profile measurement.

In addition to mounting and securing the wafer 40 which supports the one or more pressure-sensitive devices 42, the testing stage 10 can also be used for forming a pressure chamber that is below and in fluid communication with both the pressure sensitive devices and with a pressure source 32. The pressure source 32 can be used to modify the pressure inside the pressure chamber to create a pressure differential between the upper and lower surfaces of the pressure-sensitive devices to reveal some property or response of the devices. Thus, the testing stage 10 can serve to present the pressure-sensitive devices 42, while under pressure, for measurement and analysis by the surface profile measurement apparatus 104.

A basic concept for one representative embodiment of the testing stage 10 is illustrated in FIGS. 3a-3d. The outer perimeter of the testing stage may have any general shape, including circular, square and rectangular shapes, etc. The platform of the testing stage can have an upper surface 12 that is configured to accommodate the semiconductor or silicon wafer containing one or more pressure-sensitive devices for testing, as the pressure-sensitive devices amenable to such analysis include those based upon diaphragms micromachined in wafers of silicon.

At least one endless groove 14 can be situated on the upper surface 12 of the platform, which can be substantially flat. This endless groove can be configured to hold an endless support gasket 16 that serves to support the wafer above the upper surface. The endless support gasket can have a size and shape that is substantially similar to that of the endless groove in which it is to rest, as well as a cross-sectional profile suited to supporting a wafer above the upper surface 12 of the platform. Accordingly, the gasket should generally have a cross-sectional thickness that is greater than the depth of the groove in which it rests. Additionally, although the gasket contact areas on the upper surface 12 of the platform can often be grooves, flat designated areas can also be suitable as long as a seal can be maintained. For example, designated areas can be identified on the upper surface by surface indicia (surface or engraved marks) or merely approximated visually based on the location of the pressure ports 20.

As shown in the figures, both the endless groove 14 and the endless support gasket 16 can have a shape that substantially corresponds to that of the outer edge of the wafer. Silicon wafers 40 used in fabricating microdevices are commonly disc-shaped with a wafer flat that is used for manipulating and precisely orientating the wafer during the fabrication process. Thus, in accordance with a more particular aspect of the invention, the endless groove 14 and endless support gasket 16 can be generally circular in shape with a flat edge corresponding to the wafer flat typically found with silicon wafers.

The endless support gasket 16 may be made of any material having sufficient solidity and hardness to provide support to a wafer. Such materials include silicone, rubber, plastic, and metal. A material may be desired that shows a sufficient degree of elastic deformation and resilience after a wafer has been pressed down and secured against it, such as rubber or silicone. In a particular embodiment, the endless support gasket can made from silicone.

Securing the wafer 40 above the upper surface 12 of the platform can create an airtight seal between the wafer and the endless support gasket 16 to form a pressure chamber 18 between the bottom surface of the wafer and the upper surface of the platform. This pressure chamber can be located directly below and in fluid communication with the pressure-sensitive devices 42, so that the bottom surfaces of the devices are directly exposed to variations in pressure inside the pressure chamber. Once properly positioned against the sealing endless support gasket 16, the wafer 40 can secured to the testing stage with a ring clamp 36 corresponding to an outer edge of the wafer, and which can be securable to the platform with machine screws 38 threaded into screw holes 26 formed into the upper surface. Alternatively, the wafer can be secured to the testing stage by way of a vacuum device operatively connected to the pressure port 20 and configured to apply a negative pressure to the pressure chamber 18 under the wafer 40 to pull the wafer towards the upper surface 12 of the platform.

The semiconductor or silicon wafer 40 used with the testing stage 10 may be the original uncut wafer of silicon into which the one or more pressure-sensitive devices 42 to be tested were formed, grown, and/or machined. As multiple pressure-sensitive devices can often be created in one wafer, the use of the present invention allows for many or all of the devices to be tested at once. In another aspect, however, it may be desirable to test a single device that has already been separated from the wafer. In this case, a dummy wafer or substrate of some other material may be used, where the dummy wafer is configured to securely accommodate the pressure-sensitive device. Once mounted to the dummy wafer, the device can be tested by securing the dummy wafer onto the testing stage.

Testing with the testing stage 10 involves applying pressure to the pressure-sensitive devices 42, usually by applying a measured and discrete pressure to the pressure chamber 18 located between the wafer 40 and the upper surface 12 of the platform. The pressure can be applied through one or more pressure ports 20 formed into the upper surface, and communication with these pressure ports can be achieved through an interior passage 22 and access port 24 to which a source of pressure 32 (e.g. compressor, gas cylinder, etc.) may be connected via a pressure hose 30.

Figures 3A, 3B, 3C, 3D:
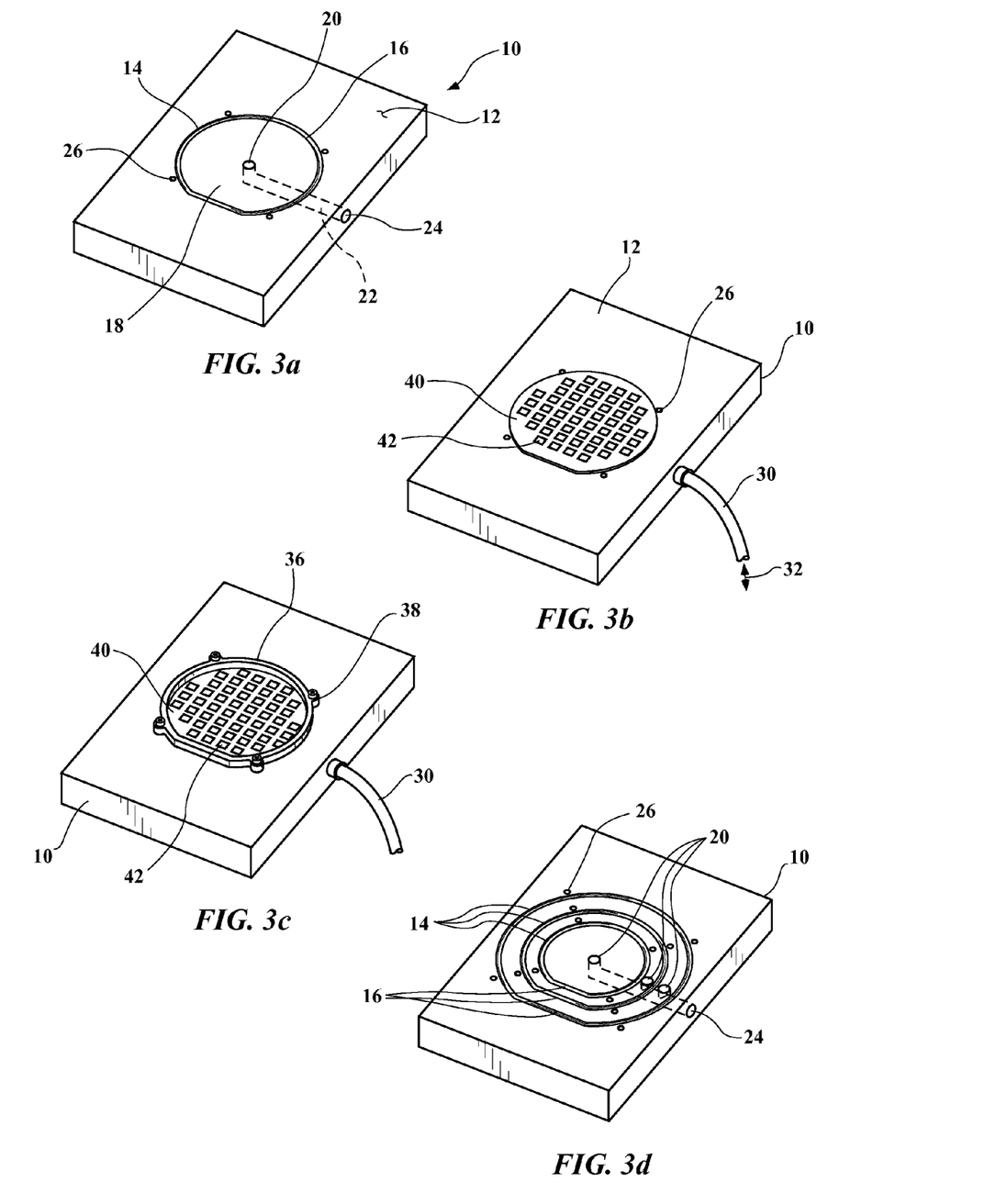
FIGS. 3a-3d illustrate perspective views of a testing stage for testing pressure-sensitive devices, in accordance with the embodiment of FIG. 2.

As illustrated in FIG. 3d, the testing stage 10 can further comprises a platform with an upper surface 12 configured to accommodate wafers 40 of various sizes. To facilitate testing of wafers having various sizes, the platform may have a plurality of grooves 14 arranged concentrically on its upper surface 12. More specifically, the plurality of grooves may be sized to accommodate a plurality of wafer sizes. In a particular embodiment, the platform can include a plurality of grooves sized to accommodate wafers from about 2 to about 8 inches in diameter. Unused gaskets can typically be removed from interior positions, although such may alternatively be left in place to selectively support portions of the wafer, depending on the desired testing conditions.

Pressure (including vacuum) can be applied to the semiconductor or silicon wafer 40 by way of one or more pressure ports 20 formed into the upper surface. With the representative embodiment configured for multiple wafer sizes (as exemplified in FIG. 3d), the testing stage 10 can have a plurality of such ports. It is to be appreciated, however, that testing platforms can also be formed to accommodate a single wafer size, e.g. having a single groove-gasket combination and one or more ports. (FIGS. 3a-3c).

In order to apply pressure to a wafer supported by a support gasket, one or more pressure ports 20 can be located interior of the endless groove 14 and/or endless support gasket 16 (e.g. more centrally on the upper surface 12 than the gasket). The pressure ports can each be connected to a common interior passage 22 having an access port 24 through which a pressure source 32 may provide the pressure needed for testing, so that the plurality of pressure ports share the common access port and are in fluid communication to one another. Alternatively, each pressure port may be connected to an access port without having any functional communication with other pressure ports, in order to allow for independent pressure control of each access port.

The pressure ports 20 can be disposed on the testing stage 10 so as to apply a pressure to the pressure chamber 18 disposed between the underside of the wafer 40 and the upper surface 12 of the platform. The pressure source and pressure ports can each be configured to provide the type of pressure needed for testing the pressure-sensitive device. In one embodiment, the pressure source 32 can be configured to apply a positive pressure to the underside of the wafer. In an alternative embodiment, the pressure source 32 can be configured to apply a negative pressure (vacuum) to the underside of the wafer. Accordingly, the pressure source in each respective embodiment is a positive pressure source or a source of vacuum. Examples of positive pressure sources include compressors and canisters of pressurized gas. Negative pressure may be provided by a vacuum line through a regulator.

In using the testing stage 10 to test devices by applying pressure, it is important that the semiconductor or silicon wafer 40 containing the pressure-sensitive devices 42 be secured to the testing stage, especially when applying positive pressure. This not only prevents the wafer from being dislodged by the pressure, but it can also serve to keep the devices stable so that their responses may be monitored by measuring or imaging equipment. Accordingly, the testing stage can also include a means for securing the wafer containing a pressure-sensitive devices above the upper surface 12 of the platform. In one aspect of the present invention, such a means can include a ring clamp 36, the size and shape of which corresponds to the outer edge and wafer flat of the wafer 40, and which is securable to the platform. The clamp can include one or more fasteners 38 by which it is attached to the upper surface of the platform, and thereby maintain sufficient downward pressure on the wafer.

Such a securing means can also serve to keep the wafer stable, and is particularly useful when positive pressure is applied underneath the wafer. However, ring clamps 36 can also be used in negative pressure testing applications. For negative pressure applications, the type of pressure used has the added benefit of pulling the wafer 40 down toward the upper surface 12. This seats the wafer more firmly against the support gasket 16 on which it rests. Therefore, in a particular embodiment, the means for securing the wafer can include a vacuum device operatively connected to the pressure ports and configured to apply negative pressure to the wafer.

Figure 4:
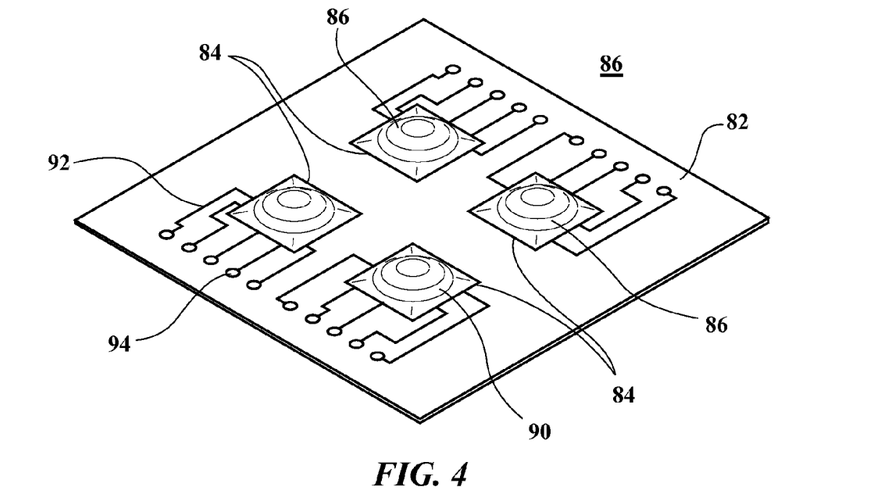
FIG. 4 illustrates a perspective view of a pressure-sensitive device undergoing testing, in accordance another representative embodiment of the present invention.

Illustrated in FIG. 4 is another representative embodiment of the present invention, in which each pressure-sensitive device 84 can include an electronic sensor 90 or sensors mounted or integrated into the surface 86 of the device, which sensors can provide an electrical output or signal proportional its deflection. The electronic sensor 90 can also be formed or integrated into the structure of the pressure-sensitive device 84 itself The electronic sensor can often be a piezoresistive element, although other features could also be suitable. As further shown in FIG. 4, one or more of the instrumented pressure-sensitive devices can be grouped together on a transducer chip 82, which can then be supported by a more generalized substrate 80. Electrical leads 92 can be routed away form the electronic sensors 90 to junctions 94, which in turn can couple the electrical output or signal from the pressure-sensitive devices 84 from the transducer chip 82 to the supporting substrate 80, and from thence to output terminals 96. As can be appreciated by one of skill in the art, a connector 98 attached to the output terminals 96 allows the electrical signals from the pressure-sensitive devices to be monitored and/or recorded. Strain gauges are one class of sensor which can perform this function, but other sensor types and measurement technologies are also possible and are considered to fall within the scope of the present invention.

In such circumstances it can by highly desirable to measure the electrical output of the electronic sensors (e.g. including changes in an applied voltage) simultaneously with measuring the surface profile of the deflected pressure-sensitive device. Consequently, illustrated in FIG. 5 is another representative embodiment 102 of the system for the testing and analysis of pressure-sensitive devices or microdevices that includes a means for measuring the output of the electronic sensor simultaneous with the measurement of the surface profile.

Similar to the embodiment described above, system 102 can include a surface profile measurement apparatus 104 for measuring the profile of the outer surfaces 86 of the deflected pressure sensitive devices 84 which are formed into transducer chips 82, and which in a representative embodiment can comprise a non-contacting optical profilometer. The system can also include the moveable test stand 110 located proximate to the surface profile measurement apparatus 104, to which the assembled testing stage 50 and substrate 80 can be attached. A pressure source 72 can be coupled to the testing stage 50 via an inlet pressure hose 70, and which in one representative embodiment can further include an outlet hose 74 coupled to an outlet valve 76 and pressure gauge 78, which outlet valve and pressure gauge can allow for the precise control and measurement of the pressure inside pressure chambers located between the lower surface of the substrate 80 and the upper surface of the testing stage 50.

Figure 5:
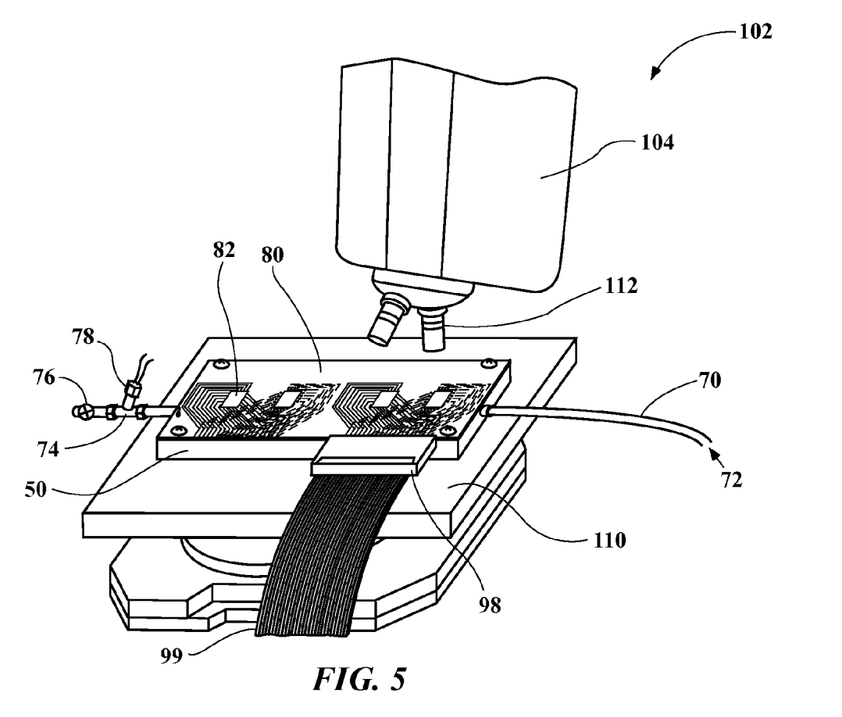
FIG. 5 illustrates a perspective view of a system for testing a pressure-sensitive device, in accordance with another representative embodiment of the present invention.

As further shown in FIG. 5, a connector 98 and attached ribbon cable 99 can be attached to output terminals located on the edge of the substrate 80, to direct the electrical signals generated by the electronic sensors 90 in the pressure-sensitive devices 84 to additional electrical instrumentation (not shown) for monitoring and/or recording, as can be appreciated by one of skill in the art.

During the testing process, the pressure source 72 can be used to modify the pressure inside the pressure chambers to create a pressure differential between the upper and lower surfaces of the pressure-sensitive devices 84 to reveal some property or response of the devices. Thus, the testing stage 50 can serve to present the pressure-sensitive devices 84, while under pressure, for measurement and analysis by the surface profile measurement apparatus 104. And with the attached connector and ribbon cable leading to the additional electrical instrumentation, the system 102 also allows for the additional measurement the output of the electronic sensors 90 simultaneous with the measurement of the surface profile.

Figure 6A:
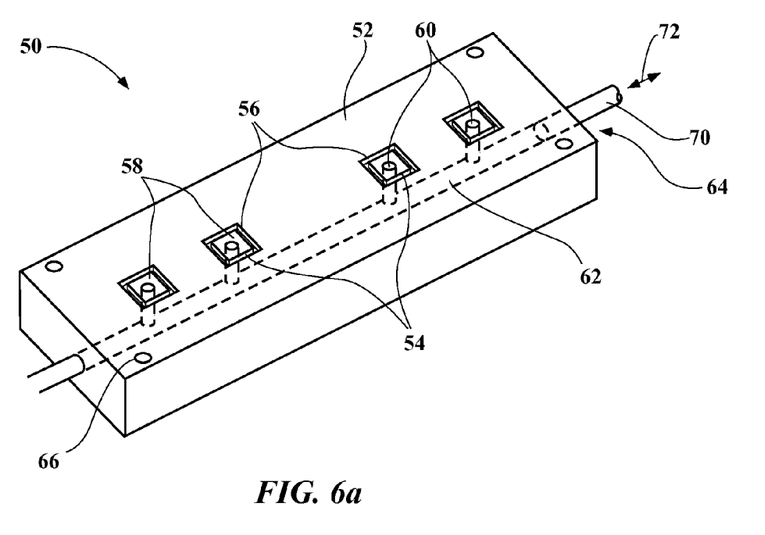
FIGS. 6a-6b illustrate perspective views of a testing stage for testing pressure-sensitive devices, in accordance with the embodiment of FIG. 5.
Figure 6B:
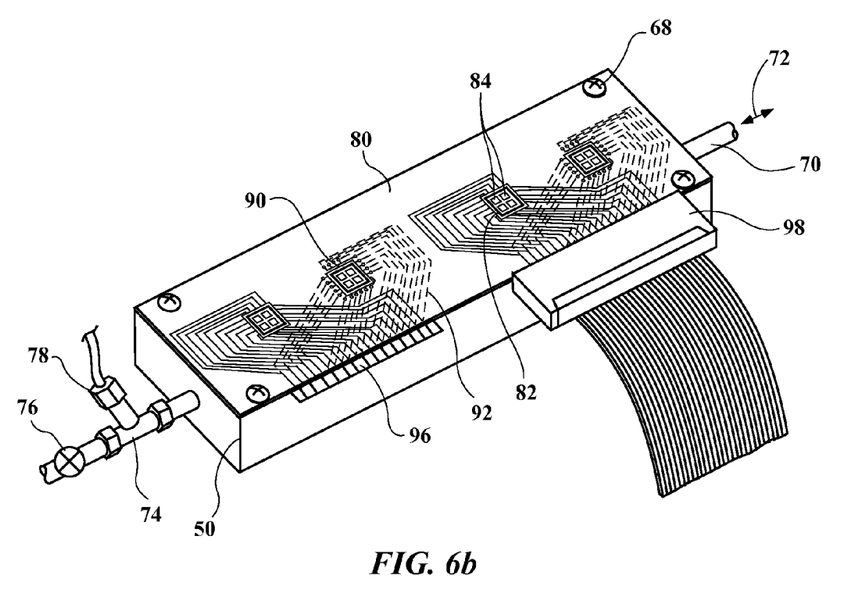

The concept for one representative embodiment of the testing stage 50 for mounting a substrate 80 that supports a plurality transducer chips 82 having one or more pressure sensitive devices 84 with integrated electronic sensors 90 is illustrated in FIGS. 6a-6b. The testing stage 50 can be used to mount and secure the generalized substrate 80 and for forming one or more pressure chambers. As shown in FIG. 6a, the testing stage 50 can include a plurality of endless grooves 54 and endless support gaskets 56 formed into the upper surface 52 of the platform that are non-concentric, and which instead are spaced apart and across the upper surface of the platform to form the pressure chambers 58 which correspond to the individual locations of the transducer chips 82 holding the pressure-sensitive devices 84. Threaded screw holes 66 can also be formed into the upper surface 52 of the platform for attaching the substrate 80.

Each endless support gaskets 56 can have a size and shape that is substantially similar to that of the endless groove 54 in which it is to rest, as well as a cross-sectional profile suited to supporting the substrate 80 above the upper surface 52 of the platform. Accordingly, the gasket can have a cross-sectional thickness that is greater than the depth of the groove in which it rests. Additionally, although the gasket contact areas on the upper surface 52 of the platform can often be grooves, flat designated areas can also be suitable as long as a seal can be maintained. For example, designated areas can be identified on the upper surface by surface indicia (surface or engraved marks) or merely approximated visually based on the location of the pressure ports 60.

As shown in FIG. 6a, both the endless grooves 54 and the endless support gasket 56s can have a shape that substantially corresponds to the shape of individual transducer chip 82 supported by the substrate 80. Thus, securing the substrate 80 to the testing stage 50 can result in airtight seals being established between the bottom surface of the substrate and each support gasket 56, to form a plurality of pressure chambers 58 located directly below and in fluid communication with the pressure-sensitive device 84, so that the bottom surfaces of the devices are directly exposed to variations in pressure inside the pressure chambers 58. In one aspect of the present invention, the substrate 80 can be secured directly to the testing stage with machine screws 68 threaded into screw holes 66 formed into the upper surface.

As can be appreciated, each of the pressure chambers 58 can also be provided with at least one pressure port 60 to place the pressure chambers, and hence the pressure-sensitive devices, in fluid communication with a pressure source 72. The pressure ports can each be connected to a common interior passage 62 having an inlet port 64 through which a pressure source 72 may provide the pressure needed for testing, so that the plurality of pressure ports 58 share the common inlet port and are in fluid communication to one another. Alternatively, each pressure port 60 may be connected to an inlet port without having any functional communication with other pressure ports, in order to allow for independent pressure control of each pressure chamber 58.

A pressure source 72 can be coupled to the testing stage 50 via an inlet pressure hose 70. In the representative embodiment shown in FIG. 6b, the testing stage can also include an outlet hose 74 coupled to an outlet valve 76 and pressure gauge 78, which outlet valve and pressure gauge can allow for the precise control and measurement of the pressure inside pressure chambers located between the lower surface of the substrate 80 and the upper surface of the testing stage 50. Furthermore, the pressure source can be configured to allow introduction of liquids for testing of hydrogel adsorption of target compounds adjacent the membranes and associated diffusion of target chemical compounds. Thus, the system can be effectively used to test the devices in gas and liquid environments. For example, many of the tested devices can be designed for use as sensors in detection of chemical compounds in fluids, e.g. blood, water, etc.

Also shown in FIG. 6b are the one or more of the instrumented pressure-sensitive devices 84 that can be grouped together on a transducer chip 82, and which can in turn be supported by the substrate 80. Electrical leads 92 can be routed away form the electronic sensors 90 to couple the electrical output or signal from the pressure-sensitive devices 84 from the transducer chip 82 to the supporting substrate 80, and from thence to output terminals 96. As can be appreciated by one of skill in the art, a connector 98 attached to the output terminals 96 can allow the electrical signals from the pressure-sensitive devices to be monitored and/or recorded by additional electrical instrumentation (not shown), such as analog or digital analyzers and tape recorders.

As described above, a method of testing the pressure-sensitive devices can comprise utilizing the above testing and analysis system in which the testing stage and wafer/substrate are situated in functional relationship with a surface profile measurement apparatus 104 designed for measuring properties of such devices. In a particular embodiment, the apparatus is an optical profilometer. Optical profilometers typically utilize various approaches to optically characterize the topology of specimens, including interferometry, confocal microscopy, and pattern projection methods. Coupled with a computer interface, optical profilometers provide visual displays of specimen surfaces as well as qualitative data analysis.

Figure 7:
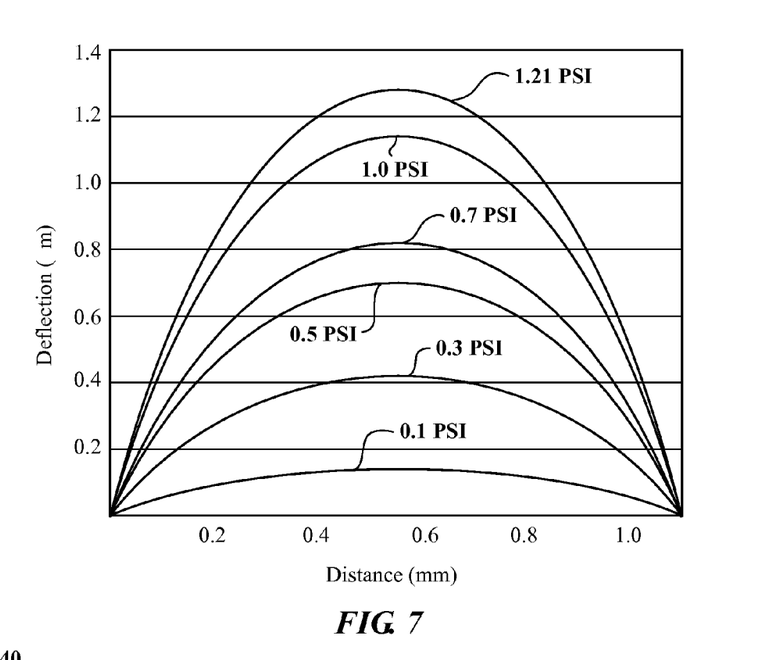
FIG. 7 is a representative graph of test data plotting the deflection across a diaphragm as a function of positive pressure applied below the diaphragm.

Illustrated in FIG. 7 are the results of one such testing procedure conducted on a pressure-sensitive device or diaphragm which was coated with 40 nm of sputtered Al to improve visibility. The figure shows the profile of the diaphragm deflected under positive testing pressures of 0.10, 0.30, 0.51, 0.70, 1.00, and 1.21 psi respectively, as measured with a ZYGO® optical profilometer. As can be appreciated, testing and analysis system of the present invention can also facilitate the measurement of other properties such as Young's modulus and residual stress consistent with known approaches such as, but not limited to, the test described in Mitchell et al., "Examination of Bulge Test for Determining Residual Stress, Young's Modulus, and Poisson's Ratio of 3C-SiC Thin Films," Journal of Aerospace Engineering, April 2003, pp. 46-54 which is incorporated herein by this reference.

Pressure-sensitive devices are also amenable to coating with thin films. Such films may be applied to confer a desired property to the device itself Conversely, the pressure-sensitive device may serve as a platform for the thin film for purposes of analyzing properties of the film. Accordingly, the systems and methods of the present invention may also be applied to pressure-sensitive devices to which thin films have been applied.

With the testing and analysis systems of the present invention, furthermore, the profilometers can be used to measure deflections and curvature across thin film diaphragms in three dimensions. This gives a much richer picture of the deflection and movements of the devices or films. In one aspect of the present invention, wafers can be produced that have a uniform distribution of diaphragms in various sizes. These diaphragms can then be deposited with thin films for investigation into their mechanical properties (Young's modulus, residual stress). The measurements occur very quickly on the order of seconds. The method can also measure deposition uniformity across the wafer by studying/comparing the diaphragms in different locations.

Figure 8:
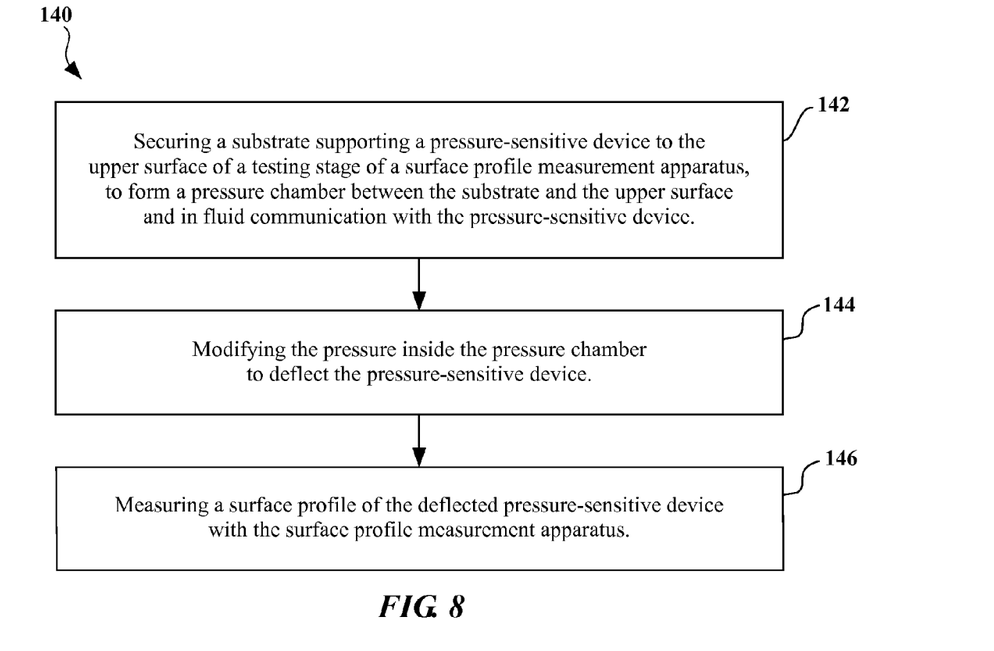
FIG. 8 is a flowchart depicting a method of analyzing a pressure-sensitive device, in accordance with a representative embodiment of the present invention.

Illustrated in FIG. 8 is a method 140 of analyzing a pressure-sensitive device, in accordance with one representative embodiment of the present invention. The method 140 includes the operation of securing 142 a substrate supporting the pressure-sensitive device to an upper surface of a testing stage of a surface profile measurement apparatus, to form a pressure chamber between the substrate and the testing stage, and in fluid communication with the pressure-sensitive device. The method 140 further includes the steps of modifying 144 the pressure inside the pressure chamber to deflect the pressure-sensitive device, and measuring 146 the surface profile of the deflected pressure-sensitive device with the surface profile measurement apparatus.

Figure 9:
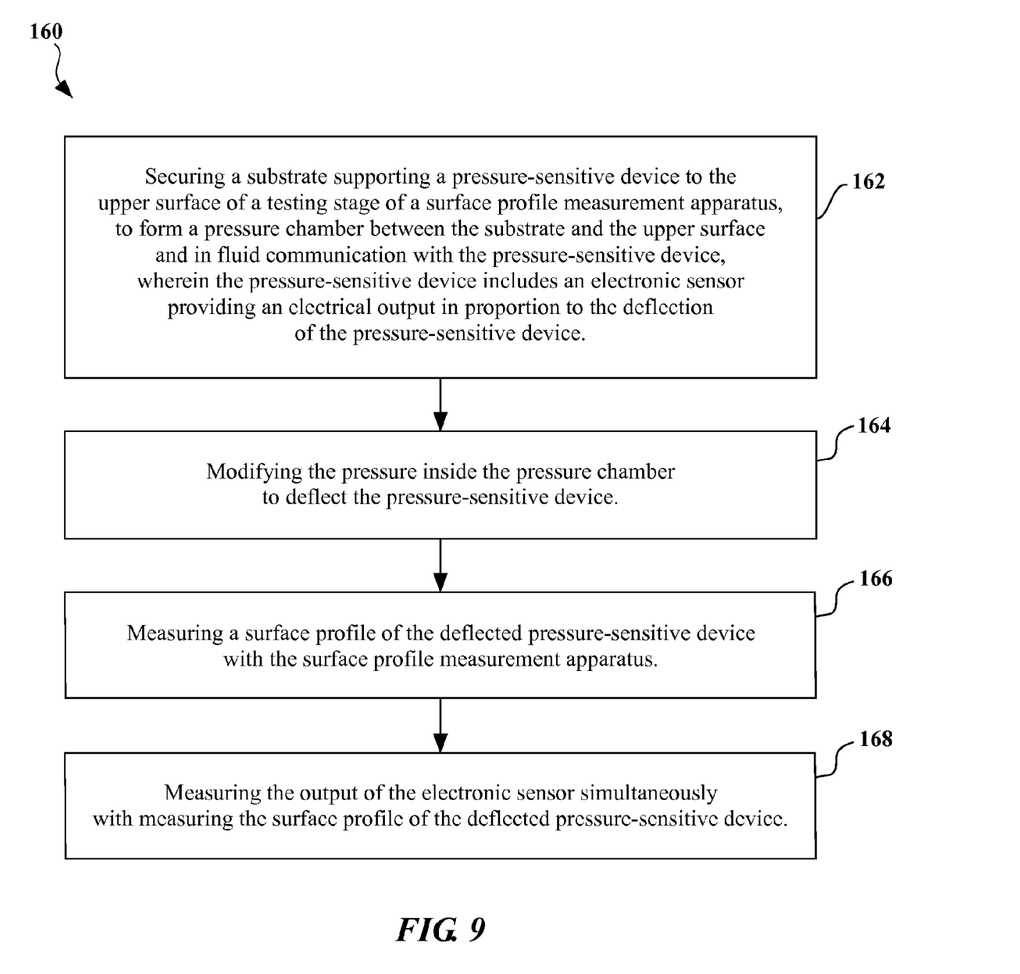
FIG. 9 is a flowchart depicting a method of analyzing a pressure-sensitive device, in accordance with another representative embodiment of the present invention

Illustrated in FIG. 9 is a method 160 of analyzing a pressure-sensitive device, in accordance with another representative embodiment of the present invention. The method 160 includes the operation of securing 162 a substrate supporting the pressure-sensitive device to an upper surface of a testing stage of a surface profile measurement apparatus, to form a pressure chamber between the substrate and the testing stage, and in fluid communication with the pressure-sensitive device, and wherein the pressure-sensitive device includes an electronic sensor providing an electrical output in proportion to the deflection of the pressure-sensitive device. The method 160 further includes the steps of modifying 164 the pressure inside the pressure chamber to deflect the pressure-sensitive device, measuring 166 the surface profile of the deflected pressure-sensitive device with the surface profile measurement apparatus, and measuring 168 the output of the electronic sensor simultaneously with measuring the surface profile of the deflected pressure-sensitive device The foregoing detailed description describes the invention with reference to specific representative embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

More specifically, while illustrative representative embodiments of the invention have been described herein, the present invention is not limited to these embodiments, but includes any and all embodiments having modifications, omissions, combinations (e.g., of aspects across various embodiments), adaptations and/or alterations as would be appreciated by those in the art based on the foregoing detailed description. The limitations in the claims are to be interpreted broadly based on the language employed in the claims and not limited to examples described in the foregoing detailed description or during the prosecution of the application, which examples are to be construed as non-exclusive. For example, in the present disclosure, the term "preferably" is non-exclusive where it is intended to mean "preferably, but not limited to". Any steps recited in any method or process claims, furthermore, may be executed in any order and are not limited to the order presented in the claims. Accordingly, the scope of the invention should be determined solely by the appended claims and their legal equivalents, rather than by the descriptions and examples given above.

What is claimed is:

1. A testing and analysis system for a pressure-sensitive device, comprising:
  a testing stage including:
    a platform having an upper surface;
    at least one endless groove situated on the upper surface;
    an endless support gasket located in the endless groove;
    at least one pressure port located on the upper surface, wherein the pressure port is located interior to the endless groove; and
    a means for securing a substrate above the upper surface;
  the substrate supporting a pressure-sensitive device, wherein the substrate is secured above the upper surface and in contact with the endless support gasket to form a pressure chamber between the substrate and the upper surface and in fluid communication with the pressure-sensitive device;
  a pressure source operatively connected to the at least one pressure port and configured to modify a pressure inside the pressure chamber and deflect the pressure-sensitive device; and
  a surface profile measurement apparatus for measuring a surface profile of the deflected pressure sensitive device.

2. The system of claim 1, wherein the pressure sensitive device further comprises an electronic sensor providing an electrical output in proportion to the deflection of the pressure-sensitive device.

3. The system of claim 2, further comprising a means for simultaneously measuring the output of the electronic sensor with the measurement of the surface profile of the deflected pressure sensitive device.

4. The system of claim 2, wherein the surface profile measurement apparatus is a non-contacting optical profilometer.

5. The system of claim 1, wherein the means for securing the substrate includes a ring clamp corresponding to an outer edge of the substrate and securable to the platform.

6. The system of claim 5, wherein the substrate is secured above the upper surface at least in part by the negative pressure.

7. The system of claim 6, wherein the plurality of grooves are sized to correspond to a plurality of substrate sizes.

8. The system of claim 6, wherein each endless groove is substantially circular with a substrate flat.

9. The system of claim 1, wherein the pressure source is configured to apply a negative pressure to the pressure chamber below the substrate to deflect the pressure-sensitive device downwards.

10. The system of claim 1, wherein the pressure source is configured to apply a positive pressure to the pressure chamber below the substrate to deflect the pressure-sensitive device upwards.

11. The system of claim 1, wherein the at least one endless groove in the upper surface of the platform further comprises a plurality of grooves and a plurality of pressure ports, wherein the grooves are situated concentrically on the upper surface, and the pressure ports are arranged so that at least one pressure port is located interior to the at least one endless groove.

12. The system of claim 1, wherein an endless gasket support area is a designated portion of the upper surface corresponding to the endless support gasket.

13. The system of claim 1, wherein the endless support gasket is made from a material selected from the group consisting of silicone, rubber, plastic, metal, and combinations or composites thereof.

14. The system of claim 1, wherein the platform is made from a material selected from the group consisting of metal, plastic, wood, and combinations or composites thereof.

15. A method of analyzing a pressure-sensitive device, comprising:

securing a substrate supporting the pressure-sensitive device to an upper surface of a testing stage of a surface profile measurement apparatus, said testing stage including:
a platform having an upper surface;
at least one endless groove situated on the upper surface;
an endless support gasket located in the endless groove, wherein the substrate is secured above the upper surface and in contact with the endless support gasket to form a pressure chamber between the substrate and the testing stage, and in fluid communication with the pressure-sensitive device; and
at least one pressure port located on the upper surface, wherein the pressure port is located interior to the endless groove and operatively connected to a pressure source configured to modify a pressure inside the pressure chamber and deflect the pressure-sensitive device;
modifying the pressure inside the pressure chamber to deflect the pressure-sensitive device; and
measuring a surface profile of the deflected pressure-sensitive device with the surface profile measurement apparatus.

16. The method of claim 15, wherein the pressure-sensitive device further comprises an electronic sensor providing an electrical output in proportion to the deflection of the pressure-sensitive device.

17. The method of claim 16, further comprising measuring the output of the electronic sensor simultaneously with measuring the surface profile of the deflected pressure-sensitive device.

18. The method of claim 15, further comprising securing the substrate above the upper surface by a ring clamp corresponding to an outer edge of the substrate and securable to the platform.

19. The method of claim 15, wherein modifying the pressure further comprises applying a negative pressure to the pressure chamber below the substrate to deflect the pressure-sensitive device downwards.

20. The method of claim 15, wherein modifying the pressure further comprises applying a positive pressure to the pressure chamber below the substrate to deflect the pressure-sensitive device upwards.

* * * * *